United States Patent [19]
Konno et al.

[11] Patent Number: 4,637,930
[45] Date of Patent: Jan. 20, 1987

[54] TRANSDERMAL FORMULATION OF NICARDIPINE HYDROCHLORIDE

[75] Inventors: Yutaka Konno; Hiroitsu Kawata; Masayoshi Aruga; Takashi Sonobe, all of Saitama; Mitsuo Mitomi, Tokyo, all of Japan

[73] Assignee: Yamanouchi Pharmaceutical Co, Ltd., Tokyo, Japan

[21] Appl. No.: 696,698

[22] Filed: Jan. 31, 1985

[30] Foreign Application Priority Data

Feb. 8, 1984 [JP] Japan .................................. 59-21404
May 17, 1984 [JP] Japan .................................. 59-99371
Jul. 26, 1984 [JP] Japan .................................. 59-156288

[51] Int. Cl.⁴ ........................ A61F 13/00; A61K 9/70; A61L 15/00
[52] U.S. Cl. ..................................... 424/28; 514/356; 514/947; 604/304; 604/307
[58] Field of Search .................. 514/356, 947; 424/28; 604/304, 307

[56] References Cited

U.S. PATENT DOCUMENTS 3,485,847 12/1969 Bossert et al. ...................... 546/321
3,644,627 2/1972 Bossert et al. ...................... 514/356
4,551,467 11/1985 Wehinger et al. .................. 514/356

OTHER PUBLICATIONS

"Goodman and Gilman's The Pharmacological Basis of Therapeutics", 6th Ed., MacMillan Publishing Co., pp. 819–828 (1980) (Goodman et al).
"Remington's Pharmaceutical Sciences", 16th Ed., Mack Publishing Company (Easton, Pa.), pp. 1520–1522 and 1261 (1980).

Primary Examiner—Ronald W. Griffin
Attorney, Agent, or Firm—Burgess, Ryan & Wayne

[57] ABSTRACT

A formulation is provided for the transdermal administration of nicardipine hydrochloride. The formulation is comprised of nicardipine hydrochloride dissolved or suspended in a mixed liquid composed of an urea and at least one compound selected from the group consisting of propylene glycol, a monohydric alcohol having 2 to 4 carbon atoms, lactic acid, thioglycol, a middle chain fatty acid glyceride and a sorbitan middle chain fatty acid ester compounded with a transdermal formulation base.

12 Claims, No Drawings

TRANSDERMAL FORMULATION OF NICARDIPINE HYDROCHLORIDE

FIELD OF THE INVENTION

This invention relates to a transdermal formulation of nicardipine hdyrochloride. More particularly, the invention relates to a nicardipine hydrochloride transdermal formulation which comprises containing a nicardipine hydrochloride dissolved or suspended in a mixed liquid composed of an urea and at least one compound selected from the group consisting of propylene glycol, a monohydric alcohol having 2 to 4 carbon atoms, lactic acid, thioglycol, a middle chain fatty acid glyceride and a sorbitan middle chain fatty acid ester compounded with a transdermal formulation base.

Furthermore, the invention relates to a stable nicardipine hydrochloride transdermal formulation composed of the above-described transdermal formulation further containing a crystallizing inhibitor of nicardipine hydrochloride.

BACKGROUND OF THE INVENTION

Recently, a systemic treatment by the transdermal administration of a medicament such as nitroglycerin, scopolamine, isosorbide dinitrate, etc., has been tried. The transdermal administration has several advantages such as a simple way for administration of a drug, a long duration of efficacy, a less occurence of side effects, avoiding inactivation by a first passage effect through the liver, etc., and is one of administration methods the further application and development of which have been expected.

Nicardipine hydrochloride is a very useful compound having a cerebral vascular dilator activity, a coronary dilator activity, and an anti-hypertension activity and considering these medicinal actions, the transdermal administration can become a very effective administration method for the compound. However, different from nitroglycerin, etc., nicardipine hydrochloride itself has poor permeability in skin transport and hence an effective transdermal formulation of the compound is not obtained by applying conventional transdermal formulations to the compound as it is.

Since epidermal tissue of an animal has a barrier mechanism for preventing invasion of foreign matters, the percutaneous absorption of medicaments largely depends upon the specific properties of the medicaments and is very complicated since it is determined by the interaction among a medicament, a base, and the skin. Accordingly, it is very difficult to estimate a contrivance or preparation for promoting the percutaneous absorption of a medicament poor in percutaneous absorption from a preparation technique of a different medicament.

Under such circumstances, the inventors started the development of a transdermal formulation of nicardipine hydrochloride and as the result of various investigations, the inventors have discovered that a transdermal formulation obtained by compounding a liquid of nicardipine hydrochloride dissolved or suspended in a mixed liquid composed of at least one of the group consisting of propylene glycol, a monohydric alcohol having 2 to 4 carbon atoms, lactic acid, thioglycol, a middle chain fatty acid glyceride, and a sorbitan middle chain fatty acid ester and a urea with a transdermal formulation base is excellent in the percutaneous absorption of nicardipine hydrochloride and based on the discovery, the invention has been accomplished.

It has also been discovered that by adding a crystallizing inhibitor of nicardipine hydrochloride to the aforesaid transdermal formulation, a nicardipine hydrochloride transdermal formulation excellent in stability and percutaneous absorption is obtained.

SUMMARY OF THE INVENTION

Thus, according to this invention, there is provided a nicardipine hydrochloride transdermal formulation comprising a liquid of nicardipine hydrochloride dissolved or suspended in a mixed liquid composed of at least one of the group consisting of propylene glycol, a monohydric alcohol having 2 to 4 carbon atoms, lactic acid, thioglycol, a middle chain fatty acid glyceride, and a sorbitan middle chain fatty acid ester and a urea, said liquid being in a transdermal formulation state.

According to another embodiment of this invention the above transdermal formulation further contains a crystallizing inhibitor of nicardipine hydrochloride.

DESCRIPTION OF THE PREFERRED EMBODIMENT

The invention will be explained below in detail.

Examples of the monohydric alcohol having 2 to 4 carbon atoms for use in this invention are ethanol, propanol, isopropanol, etc. Examples of the middle chain fatty acid glyceride for use in this invention are mono- or di-esters of glycerol and fatty acids having 6 to 12 carbon atoms. Specific examples of them are caproic acid mono- or di-glyceride, caprylic acid mono- or di-glyceride, capric acid mono- or di-glyceride, and lauric acid mono- or di-glyceride. These materials may be used solely as a mixture of two or more materials. For example, a mixture of 54.3% caprylic acid mono-glyceride and 37% caprylic acid di-glyceride is commercially available as a trade name "Nikkol MGK" (made by Nikko Chemicals Co.) or a product containing more than 85% caprylic acid mono-glyceride is commercially available as a trade name "Sunsoft No. 700p-2" (made by Taiyo Kagaku K. K.). These commercially available products can be used in this invention.

As the sorbitan middle chain fatty acid ester for use in this invention, there are mono- or di-esters of sorbitol and fatty acids of 6 to 12 carbon atoms. Specific examples of these esters are sorbitan mono-caproic acid ester, sorbitan dicaproic acid ester, sorbitan monocaprylic acid ester, sorbitan dicaprylic acid ester, sorbitan monocapric acid ester, sorbitan dicapric acid ester, sorbitan monolauric acid ester, and sorbitan dilauric acid ester. They can be used solely or as a mixture of them.

The compounding amount of the middle chain fatty acid glyceride or the sorbitan middle chain fatty acid ester in the transdermal formulation of this invention is in the range of 0.5 to 20 w/w%, preferably 1 to 15 w/w%.

Also, ureas for use in this invention include urea, thiourea and the lower alkyl derivatives thereof, such as ethylurea, 1,1-dimethylurea, 1,1-diethylurea,

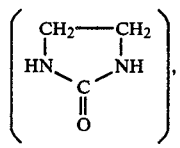

etc.

The urea is usually used as a solution or suspension in water. The compounding amount of the urea in the transdermal formulation of this invention is 0.3 to 30 w/w%, preferably 1 to 10 w/w%.

The compounding amount of the monohydric alcohol having 2 to 4 carbon atoms or thioglycol in the transdermal formulation of this invention is 0.3 to 30 w/w%, preferably 1 to 10 w/w%.

Also, the compounding amount of lactic acid is 0.3 to 10 w/w%, preferably 0.5 to 5 w/w%.

Then, propylene glycol is compounded in the transdermal formulation of this invention in an amount of 0.5 to 15 w/w%, preferably 1 to 10 w/w%. Propylene glycol has an action of increasing the solubility of nicardipine hydrochloride and a humidity retaining action, an antiseptic action, etc., as well as a function of promoting the percutaneous absorption of nicardipine hydrochloride. The proportion of nicardipine hydrochloride in the transdermal formulation of this invention is usually 1 to 20 w/w%.

The compounding components described above are uniformly mixed.

In addition, In the case of using the middle chain fatty acid glyceride or the sorbitan middle chain fatty acid ester, it is preferred to use porpylene glycol together therewith.

Now, in spite of that each of the aforesaid components has low solubility for nicardipiene hydrochloride, a mixed system of them can increase the solubility for nicardipine hydrochloride and by dispersing the solution of nicardipine hydrochloride in a transdermal formulation base, a good percutaneous absorption of nicardipine hydrochloride is obtained.

Further in the case of using the middle chain fatty acid glyceride or the sorbitan middle chain fatty acid ester, there is a heterogeneous range in which these components are not uniformly mixed according to the compounding ratios of these components but by adding nicardipine hydrochloride to a mixture of these components in the heterogeneous range, an unexpectedly uniform nicardipine hydrochloride solution can be obtained, thereby the dissolution ranges of the above-described compounding components can be enlarged and good results for the preparation of the transdermal formulation and the percutaneous absorption are obtained.

Then, there is no particualr restriction about the amount of the mixed liquid to nicardipine hydrochloride if the amount is enough to uniformly dissolve or suspend nicardipine hydrochloride in the mixture of these components and can keep the form of a transdermal formulation when the mixture is compounded to a transdermal formulation base. The amount of the mixed liquid depends upon the kind of a base to be used and other compounding components and it is preferable to control the amount of mixed liquid in consideration of the proportion of nicardipine hydrochloride (i.e., 1 to 20 w/w%))

If the concentration of nicardipine hydrohcloride is high, it sometimes happens that nicardipine hydrochloride is crystallized when the solution thereof is stored for a long period of time. For inhibition of crystallizing, compounding of polyoxyethylene-hardened castor oil, neopentyl glycol di-2-ethylhexanoate, propylene glycol didecanoate, etc., is effective. It is proper that the compounding amount of the crystallizing inhibitor is 0.5 to 10 w/w%, preferably 1 to 5 w/w%.

The transdermal formulation of this invention may further contain proper auxiliary compounds for stabilization and the desired pH.

Furthermore, for uniformly dispersing nicardipine hydrochloride in the base, an emulsifier may be compounded. As the emulsifier, nonionic surface active agents, for example, glycerol higher fatty acid esters such as glyceryl monostearate (Nikkol MGS-B, trade name, made by Nikko Chemical Co., Ltd.), polyglycerol fatty acid ester (Nikkol Decaglyn, trade name, made by Nikko Chemical Co., Ltd.), etc.; polyoxyethylene sorbitan monostearate (Tween 60, made by Kao Atlas Co., Ltd.); sorbitan higher fatty acid esters such as sorbitan monostearate (Span 60, trade name, made by Kao Atlas Co., Ltd.), etc.; polyoxyethylene monolaurate (Nikkol MYL-10, trade name, made by Nikko Chemical Co., Ltd.); polyoxyethylene lauryl ether (Nikkol BL-9EX, trade name, made by Nikko Chemical Co., Ltd.); polyoxyethylene polyoxypropylene copolymer (Pluronic F68, trade name, made by Asahi Denka Kogyo K. K.), etc., can be used. It is proper that the amount of the emulsifier is 0.5 to 10 w/w%.

There is no particular restriction about the base for use in this invention but usually white petrolatum, plastibase, silicone oils, etc., are preferred. By properly selecting the base and the compounding components, transdermal formulations such as ointment, tape, patch, cataplasm, etc., can be prepared by conventional methods.

For example, an ointment of this invention can be prepared by dissolving nicardipine hydrochloride in a mixed liquid of a urea and at least one of propylene glycol, a monohydric alcohol having 2 to 4 carbon atoms, lactic acid, thioglycol, a middle chain fatty acid glyceride, and a sorbitan middle chain fatty acid ester, gradually adding the solution to a mixture of an ointment base and an emulsifier, which was melted at 60° C. and then cooled to room temperature, until the resultant mixture becomes uniform, and sufficiently kneading the mixture. In the case of compounding a crystal deposition inhibitor therewith, the crystal deposition inhibitor is added to the ointment thus obtained followed by uniformly mixing. As the base which is used for the preparation of the ointment, the above-described oily bases are suitable.

Then, the patch of this invention is prepared as follows. That is, a carrier such as a nonwoven fabric, a paper, a cloth, a plastic film or sheet, etc., is impregnated with a liquid obtained by dissolving or suspending nicardipine hydrochloride in an aqueous solution of a urea and at least one of propylene glycol, a monohydric alcohol having 2 to 4 carbon atoms, lactic acid, thioglycol, a middle chain fatty acid glyceride, and a sorbitan middle chain fatty acid ester, or the aforesaid liquid is gelled and applied on a flexible metal foil and spread and, if necessary, an adhesive layer is formed thereon, to form a patch form.

In this case, an antiseptic (e.g., paraben, etc.,), a humidity retaining agent (e.g., glycerol, etc.,), a suspending agent (e.g., silicic anhydride, Aerosil, trade name), etc., may be compounded.

Then, a percutaneous absorption test and a storage stability test about the transdermal formualtions of this invention are shown below together with the results thereof.

(1) Percutaneous absorption test in guinea pig:

Guinea pigs (weighing about 400 g), the back of which was shaved by an electric clipper and a depilatory cream, were used. About 1 g of each of the ointments obtained in Examples 1, 2, 3, 9, 10, 11, 12, 13 and 14 described hereinbelow placed in a plastic container (about 10 cm$^2$ in area) was stuck to the shaved skin of the guinea pig, and after covering the ointment with parafilm, it was fixed by a gum tape. After 5 hours since the transdermal administration of the ointment, blood was collected and the blood concentration of nicardipine hydrochloride was measured according to a Higuchi et al's method ("Journal of Chromatography", 110, 301(1975)). The results are shown below.

| Test ointment | Result" Plasma concentration (ng/ml) of nicardipine hydrochloride |
|---|---|
| Example 1 | 16.3 |
| Example 2 | 29.0 |
| Example 3 | 64.0 |
| Example 4 | 70.3 |
| Example 9 | 79.7 |
| Example 10 | 57.5 |
| Example 11 | 42.0 |
| Example 12 | 73.8 |
| Example 13 | 60.0 |
| Example 14 | 65.0 |
| Reference sample* | 5.7 |

*The ointment used in the comparison test was prepared by melting 186.4 g of white vaseline and 9.1 g of Nikkol MGS-B at about 60° C., directly adding 4.5 g of nicardipine hydrochloride to the molten mixture in a kneader, and kneading well the mixture.

(2) Stability test (the test about the crystal deposition of nicardipine hydrochloride in ointments):

The extent of the crystal deposition of nicardipine hydrochloride was observed using a polarising microscope about the ointments prepared in Examples 13 to 16 in both the state directly after the preparation thereof and after storing for one month at room temperatuer. The results show that the crystal deposition was very slight in Examples 14 to 16 as compared to Example 13.

The following examples are intended to illustrate the present invention but not to limit in any way.

EXAMPLE 1

After melting 159.1 g of white petrolatum and 9.1 g of Nikkol MGS-B at about 60° C., the molten mixture was transferred into a kneader. Then, a solution of 4.5 g of nicardipine hydrochloride dissolved in 27.3 g of a mixed solvent of urea/pure water/ethanol (1:1:1 by weight ratio) was gradually added to the mixture with stirring and the resultant mixture was kneaded to provide an ointment.

EXAMPLE 2

After melting 150 g of white petrolatum and 9.1 g of Nikkol MGS-B at about 60° C., the molten mixture was transferred into a kneader and then by following the same procedure as Example 1 using a solution of 4.5 g of nicardipine hydrochloride dissolved in 36.4 g of a mixed solvent of urea/pure water/ethanol/propylene glycol (1:1:1:1 by weight ratio), an ointment was obtained.

EXAMPLE 3

After melting 159.1 g of white petrolatum and 9.1 g of Nikkol MGS-B, the molten mixture was transferred into a kneader and then, by following the same procedure as Example 1 using a solution of 4.5 g of nicardipine hydrochloride dissolved in 27.3 g of a mixed solvent of urea/pure water/lactic acid (1:1:1 by weight ratio), an ointment was obtained.

EXAMPLE 4

After melting 150 g of white petrolatum and 9.1 g of Nikkol MGS-B at about 60° C., the molten mixture was transferred into a kneader and then by following the same procedure as Example 1 using a solution of 4.5 g of nicardipine hydrochloride dissolved in 36.4 g of a mixed solvent of urea/pure water/lactic acid/propylene glycol (1:1:1:1 by weight ratio), an ointment was obtained.

EXAMPLE 5

After melting 150 g of white petrolatum and 9.1 g of Nikkol MGS-B at about 60° C., the molten mixture was transferred into a kneader and then by following the same procedure as Example 1 using a solution of 4.5 g of nicardipine hydrochloride dissolved in 36.4 g of a mixed solvent of urea/pure water/lactic acid/ethanol (1:1:1:1 by weight ratio), an ointment was obtained.

EXAMPLE 6

After melting 163 g of white petrolatum and 9.1 g of Nikkol MGS-B at about 60° C., the molten mixture was transferred into a kneader and then by following the same procedure as Example 1 using a solution of 4.5 g of nicardipine hydrochloride dissolved in 22.8 g of a mixed solvent of thioglycol/urea/pure water (1:1:0.5 by weight ratio), an ointment was obtained.

EXAMPLE 7

A mixture of 40 g of diisopropyl adipate, 45.5 g of a middle chain fatty acid triglyceride (ODO, trade name, made by Nisshin Seiyu K. K.), 40 g of isopropyl myristate, and 10 g of glyceryl monostearate (Nikkol MGS-B) was heated to about 50° C. to provide liquid A.

Also, 4.5 g of nicardipine hydrochloride was dissolved in 40 g of a mixed liquid of lactic acid/urea/pure water/propylene glycol (1:1:1:1 by weight ratio) to provide liquid B.

Liquid A was gradually added to 20 g of Aerosil (made by Nippon Aerosil K. K.) in a kneader followed by kneading and liquid B was gradually added thereto followed by sufficiently kneading to provide an ointment.

EXAMPLE 8

A mixture of 27.5 parts of pure water, 5.0 parts of concentrated glycerol and 5.0 parts of gelatin was heated to 50° C. to provide a solution, 20.0 parts of kaolin was added to the foregoing solution followed by kneading, 2.5 parts of sodium polyacrylate and 15.0 parts of concentrated glycerol were added thereto followed by kneading, 1.0 part of polyoxyethylene sorbitan monostearate and 7.0 parts of liquid paraffin were added thereto followed by kneading, and then 10.0 parts of a previously prepared nicardipine hydrochloride solution (a solution of 0.5 part of nicardipine hydrochloride dissolved in 9.5 parts of a mixed solvent of urea/- pure water/lactic acid/propylene glycol (1:1:1:1 by weight ratio) and 7.0 parts of a natural rubber latex were added thereto followed by uniformly kneading. The kneaded mixture thus obtained was spread over flannel and after sticking a plastic film to the surface thereof, the fabric was cut into a predetermined size.

EXAMPLE 9

After melting 148.5 g of white petrolatum and 9.0 g of Nikkol MGS-B at about 60° C., the molten mixture was transferred into a kneader. Then a solution of 4.5 g of nicardipine hydrochloride dissolved in a mixed liquid of 11 g of Nikkol MGK, 9.0 g of urea, 9.0 g of pure water, and 9.0 g of propylene glycol was gradually added thereto with stirring and the mixture was kneaded to provide an ointment.

EXAMPLE 10

By following the same procedure as Example 9 except that 11 g of Sunsoft No. 700p-2 (made by Taiyo Kagaku K. K.) was used in place of 11 g of Nikkol MGK, an ointment was obtained.

EXAMPLE 11

By following the same procedure as Example 9 except that 6.0 g of Nikkol MGK and 5.0 g of Nikkol HCO-60 were used in place of 11 g of Nikkol MGK, an ointment was obtained.

EXAMPLE 12

After melting 158.3 g of white petrolatum and 9.0 g of Nikkol MHS-B at about 60° C., the molten mixture was transferred into a kneader. Then, a solution of 4.5 g nicardipine hydrochloride dissolved in a mixture of 11 g of Nikkol MGK, 4.8 g of urea, 3.2 g of pure water, 8.2 g of propylene glycol, and 1.0 g of lactic acid was gradually added to the molten mixture with stirring and the resultant mixture was kneaded to provide an ointment.

EXAMPLE 13

After melting 148.5 g of white petrolatum and 9.0 g of Nikkol MGS-B at about 60° C., the molten mixture was transfered into a kneader. Then, a solution of 4.5 g of nicardipine hydrochloride dissolved in a mixture of 11 g of Nikkol SK-10 (sorbitan monocaprirate, made by Nikko Chemicals Co., Ltd.), 9.0 g of urea, 9.0 g of pure water, and 9.0 g of propylene glycol under heating was gradually added to the molten mixture and the resultant mixture was kneaded to provide an ointment.

EXAMPLE 14

After melting 139.5 g of white petrolatum and 9.0 g of Nikkol MGS-B at about 60° C., the molten mixture was transferred into a kneader. Then, a solution of 4.5 g of nicardipine hydrochloride dissolved in a mixture of 11 g of Nikkol SK-10, 9.0 g of urea, 9.0 g of pure water, and 9.0 g of propylene glycol under heating was gradually added to the molten mixture with stirring and finally 9.0 g of propylene glycol didecanoate was added thereto followed by kneading to provide an ointment.

EXAMPLE 15

By following the same procedure as Example 14 except that neopentyl glycol di-2-ethylhexanoate was used in place of propylene glycol didecanoate, an ointment was prepared.

EXAMPLE 16

By following the same procedure as Example 14 except that Nikkol HCO-60 was used in place of propylene glycol didecanoate, an ointment was prepared.

What is claimed is:

1. A transdermal formulation containing 1 to 20 weight percent of a nicardipine hydrochloride and wherein said nicardipine hydrochloride is dissolved or suspended in a mixed liquid comprised of, based on the weight of said formulation:
   (1) 0.3 to 30 weight percent of a urea, and
   (2) at least one member selected from the group consisting of (a) 0.5 to 15 weight percent of propylene glycol, (b) 0.3 to 30 weight percent of thioglycol, (c) 0.3 to 30 weight percent of a monohydric alcohol having from 2 to 4 carbon atoms, (d) 0.3 to 10 weight percent of lactic acid, (e) 0.5 to 20 weight percent of mono- or di-esters of glycerol and fatty acids having 6 to 12 carbon atoms, and (f) 0.5 to 20 weight percent of mono- or di-esters of sorbitol and fatty acids having 6 to 12 carbon atoms, and said formulation containing a pharmaceutically acceptable carrier.

2. The transdermal formulation as claimed in claim 1, wherein the monohydric alcohol having 2 to 4 carbon atoms is ethanol.

3. The transdermal formulation as claimed in claim 1, wherein the urea is urea.

4. The transdermal formulation of claim 1 wherein said carrier is an oily base for an ointment.

5. The transdermal formulation of claim 1 wherein said carrier is an adhesive base for a tape or patch.

6. A process for the transdermal administration of nicardipine hydrochloride which comprises contacting the epidermal tissue with the transdermal formulation of claim 1.

7. The process of claim 6 wherein the transdermal formulation is contained on a tape.

8. The process of claim 6 wherein the transdermal formulation is contained on a patch.

9. A transdermal formulation containing 1 to 20 weight percent of a nicardipine hydrochloride and 0.5 to 10 weight percent of a crystallizing inhibitor for nicardipine hydrochloride, said nicardipine hydrochloride and inhibitor being dissolved or suspended in a mixed liquid comprised of, based on the weight of said formulation:
   (1) 0.3 to 30 weight percent of a urea, and
   (2) at least one member selected from the group consisting of (a) 0.5 to 15 weight percent of propylene glycol, (b) 0.3 to 30 weight percent of thioglycol, (c) 0.3 to 30 weight percent of a monohydric alcohol having from 2 to 4 carbon atoms, (d) 0.3 to 10 weight percent of lactic acid, (e) 0.5 to 20 weight percent of mono- or di-esters of glycerol and fatty acids having 6 to 12 carbon atoms, and (f) 0.5 to 20 weight percent of mono- or di-esters of sorbitol and fatty acids having 6 to 12 carbon atoms, and said formulation containing a pharmaceutically acceptable carrier.

10. The transdermal formulation as claimed in claim 9, wherein the crystallizing inhibitor of nicardipine hydrochloride is at least one compound selected from the group consisting of propylene glycol didecanoate, neopentyl glycol di-2-ethylhexanoate, and a polyoxyethylene-hardened caster oil derivative.

11. The transdermal formulation of claim 9 wherein said carrier is an oily base for an ointment.

12. The transdermal formulation of claim 9 wherein said carrier is an adhesive base for a tape or patch.

* * * * *